United States Patent [19]

Nobles

[11] Patent Number: 5,263,956
[45] Date of Patent: Nov. 23, 1993

[54] BALL JOINT FOR NEUROSURGERY

[75] Inventor: Anthony A. Nobles, Fountain Valley, Calif.

[73] Assignee: Neuro Navigational Corporation, Costa Mesa, Calif.

[21] Appl. No.: 846,000

[22] Filed: Mar. 4, 1992

[51] Int. Cl.$^5$ .................. A61B 17/00; A61B 19/00
[52] U.S. Cl. ............................. 606/130; 606/1
[58] Field of Search ................. 606/1, 108, 130; 128/653 SC; 604/116

[56] References Cited

U.S. PATENT DOCUMENTS

| | | | |
|---|---|---|---|
| 2,697,433 | 12/1954 | Zehnder | 606/130 |
| 3,017,887 | 1/1962 | Heyer | 606/130 |
| 3,115,140 | 12/1963 | Volkman | 606/130 |
| 3,457,922 | 7/1969 | Ray | 606/130 |
| 4,805,615 | 2/1989 | Carol | 606/130 |
| 4,809,694 | 3/1989 | Ferrara | 606/130 |
| 4,955,891 | 9/1990 | Carol | 606/130 |
| 5,030,223 | 7/1991 | Anderson et al. | 606/130 |
| 5,163,430 | 11/1992 | Carol | 606/130 |

Primary Examiner—Stephen C. Pellegrino
Assistant Examiner—Glenn Dawson
Attorney, Agent, or Firm—John L. Rogitz

[57] ABSTRACT

A ball joint for holding a neurosurgery tool in a predetermined orientation relative to a patient's skull has a plate that fits onto the skull. The plate is formed with a socket, and a ball is rotatably positioned in the socket. The ball, in turn, is formed with a bore, and the neurosurgery tool can be positioned in the bore to extend through the bore of the ball into the patient's brain. The ball can accordingly be rotated as appropriate to establish a predetermined orientation of the neurosurgery tool relative to the patient's skull. Set screws are provided to hold the neurosurgery tool stationary relative to the bore of the ball, and to hold the ball stationary relative to the plate. A retainer ring holds the ball against the plate.

16 Claims, 2 Drawing Sheets

BALL JOINT FOR NEUROSURGERY

FIELD OF THE INVENTION

The present invention relates generally to neurosurgery tools, and more particularly to devices for holding neurosurgery tools in a predetermined orientation relative to the skull of a patient.

BACKGROUND OF THE INVENTION

Neurosurgery, particularly neurosurgery on the brain, typically requires the precise positioning of a surgical tool within a body organ of extreme sensitivity. For example, when performing neurosurgery on the brain to excise a tumor, a surgical probe must be advanced into the brain along a precise route and precisely positioned adjacent the tumor to be excised. In brain surgery, a mispositioned or misrouted surgical probe, even if only slightly mispositioned or misrouted, can have disastrous consequences.

Not surprisingly, devices have been introduced which provide for the precise orientation and positioning of surgical tools within the brain, and which also support the surgical tools to prevent unintentional movement of the tools, once properly positioned. Several examples of such devices are set forth in *Tumor Stereotaxis*. More specifically, *Tumor Stereotaxis* discloses many types of stereotactic frames that can be fixedly attached to the skull of a patient to establish an external reference frame for the patient's brain. Additionally, the stereotactic frames disclosed in *Tumor Stereotaxis* can be used to precisely position and orient a surgical tool in the brain. More particularly, stereotactic frames typically have one or more movable arms, and at least one of the arms has a support bushing through which a surgical tool can be positioned. By positioning the surgical tool through the support bushing and then orienting the arms as desired, the surgical tool can be placed in a predetermined orientation relative to the brain.

Unfortunately, stereotactic frames have several drawbacks. For example, stereotactic frames are relatively complicated, bulky instruments. Consequently, they can interfere with the surgical procedure. Also, stereotactic frames ordinarily support the neurosurgery probe at a point that is relatively distanced from the skull of the patient. This limits the range of motion through which the probe can be pivoted, thus limiting the range of orientation of the probe vis-a-vis the skull of the patient.

Manually supporting a surgical probe in a precise orientation relative to the brain is ordinarily unacceptably cumbersome, and can result in inexact positioning of the probe. Further, existing stereotactic frames, even when used only for supporting surgical tools, interfere with the surgeon's range of motion. There is therefore the need to provide an apparatus which can hold a surgical tool in a precise predetermined orientation relative to the brain, and result in minimal interference with the surgeon's range of motion.

Thus, it is an object of the present invention to provide a relatively small, simple device for precisely orienting a surgical tool relative to a patient's brain. It is another object of the present invention to provide a device which can support a neurosurgery tool, without need of a stereotactic frame. Yet another object of the present invention is to provide a device that is easy to use and cost effective to manufacture.

SUMMARY OF THE INVENTION

An orientation tool which is small in relation to the skull is provided to hold and support a neurosurgical probe in a predetermined orientation relative to the skull. The tool has an engagement member which engages the skull and a probe guiding member that is engageable with the plate. In the preferred embodiment, the engagement member is a plate and the probe guiding member is a ball.

The preferred embodiment of the tool accordingly includes a plate which has a bottom surface that rests on the skull and generally conforms to the skull. The plate also has a top surface, and the top surface has a socket formed in it. A ball is positioned in the socket and can rotate within the socket.

To provide a passageway through which a neurosurgical probe, e.g., a guide cannula, can be inserted into the brain, the ball is formed with a bore. More specifically, a bore is drilled in the ball or formed on the ball, and the bore preferably defines an axis of the ball. As contemplated by the present invention, the plate is formed with a channel to establish communication between the bore of the ball and the patient's skull.

The neurosurgery probe can be slidably engaged with the bore and when so engaged is closely supported by the walls of the bore. Accordingly, the ball can be rotated as appropriate to establish a predetermined orientation of the bore (and, hence, the neurosurgery probe) with respect to the patient's skull. To hold the ball within the socket, a retainer ring can be fitted over the ball and fixedly attached to the plate, as by bolting.

To hold the plate onto the skull, the four bottom corners of the plate are sharpened for gripping the skull. Alternatively, small spikes are attached to the four bottom corners of the plate and extend outwardly therefrom, to grip the skull.

When the neurosurgery probe has been inserted as desired through the ball joint into the patient's brain, the probe can be "fastened" within the bore of the ball by a fastening member. In one presently preferred embodiment, a threaded orifice is formed in the ball between the bore and the ball's surface, and the fastening member is a set screw which is engaged with the orifice. The screw can be rotated to contact the neurosurgery probe within the bore and thereby prevent relative motion between the tool and ball.

Similarly, when the ball has been rotated as desired to establish the predetermined orientation of the neurosurgery tool relative to the patient's skull, the ball can be "locked" within the socket by a locking member to prevent further rotation of the ball. In the presently preferred embodiment, a threaded aperture is formed in the plate and extends from the surface of the plate to the socket. In this embodiment, the locking member is a bolt and the bolt is engaged with the aperture and can be rotated to contact the ball to thereby hold the ball stationary with respect to the plate.

The details of the operation and construction of the present invention can best be understood with reference to the accompanying drawings, in which like numerals refer to like parts, and in which:

DETAILED DESCRIPTION OF THE PREFERRED EMBODIMENT

Figure 1:
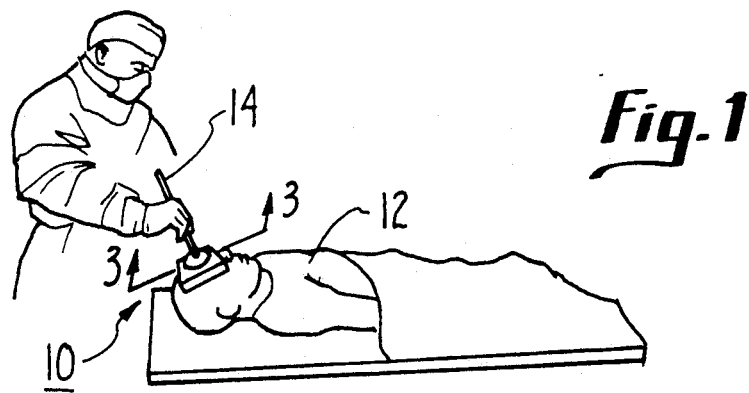
FIG. 1 is a perspective view of the ball joint of the present invention, shown in an intended neurosurgery environment.

Referring initially to FIG. 1, an orientation tool for neurosurgery is shown, generally designated 10. As shown in FIG. 1, the tool 10 can be engaged with a site on the skull of a patient 14 to a neurosurgery probe 14 along one of a plural of predetermined path into the brain of the patient 14 incident to neurosurgery on the brain of the patient 12. Specifically, the orientation tool 10 in one presently preferred embodiment is a ball joint, and the tool 10 supports a neurosurgery probe 14 in a predetermined orientation relative to the skull of the patient 12. Accordingly, the tool 10 permits the neurosurgery probe 14 to be advanced into the patient 12 along a precise, predetermined path. Also, the tool 10 holds the neurosurgery probe 14 in a predetermined position once the probe 14 has been advanced as desired into the patient 12. The probe 14 can be any device which is intended to be inserted into a patient's brain. For instance, the probe 14 can be a steel cannula.

Figure 2:
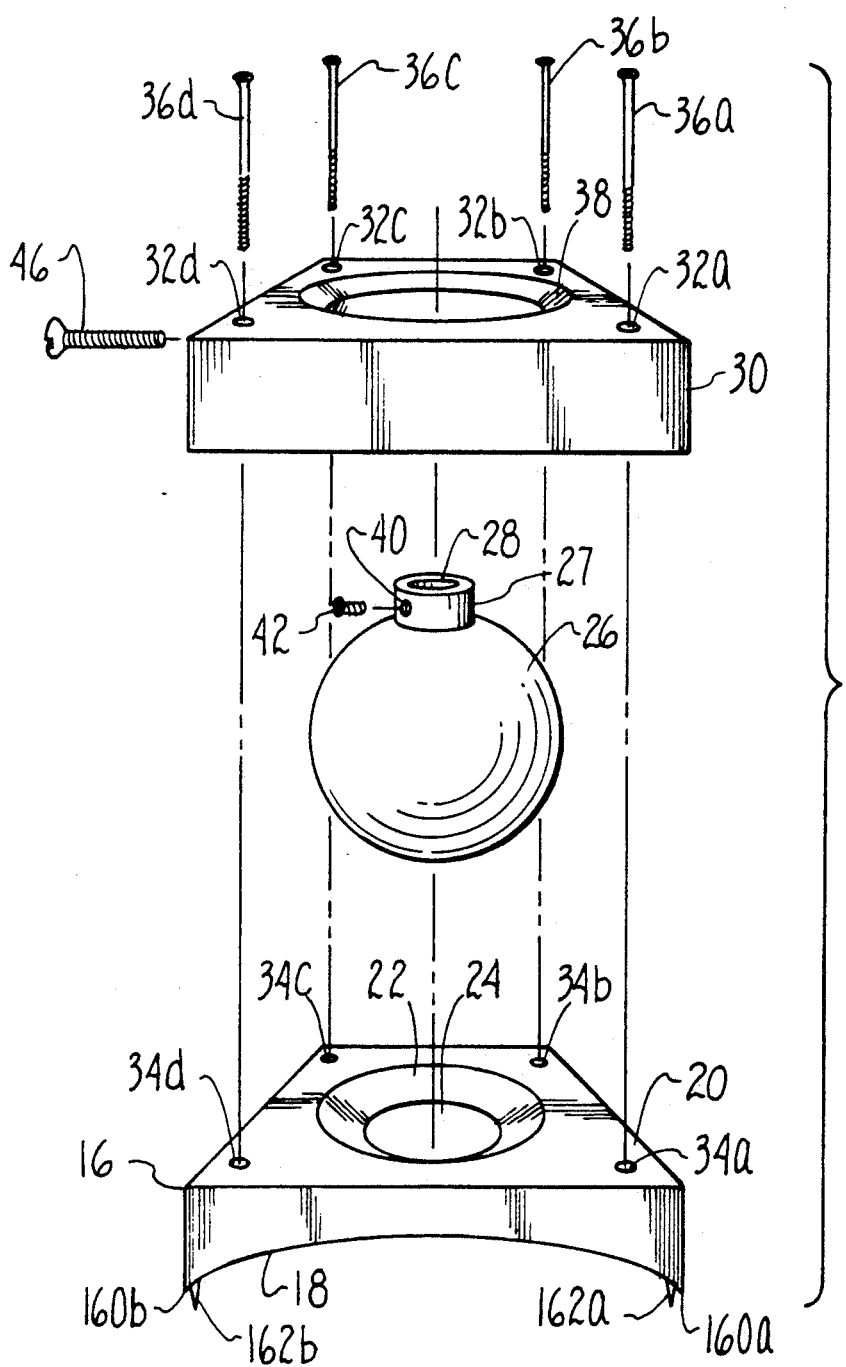
FIG. 2 is an exploded perspective view of the ball joint of the present invention.
Figure 3:
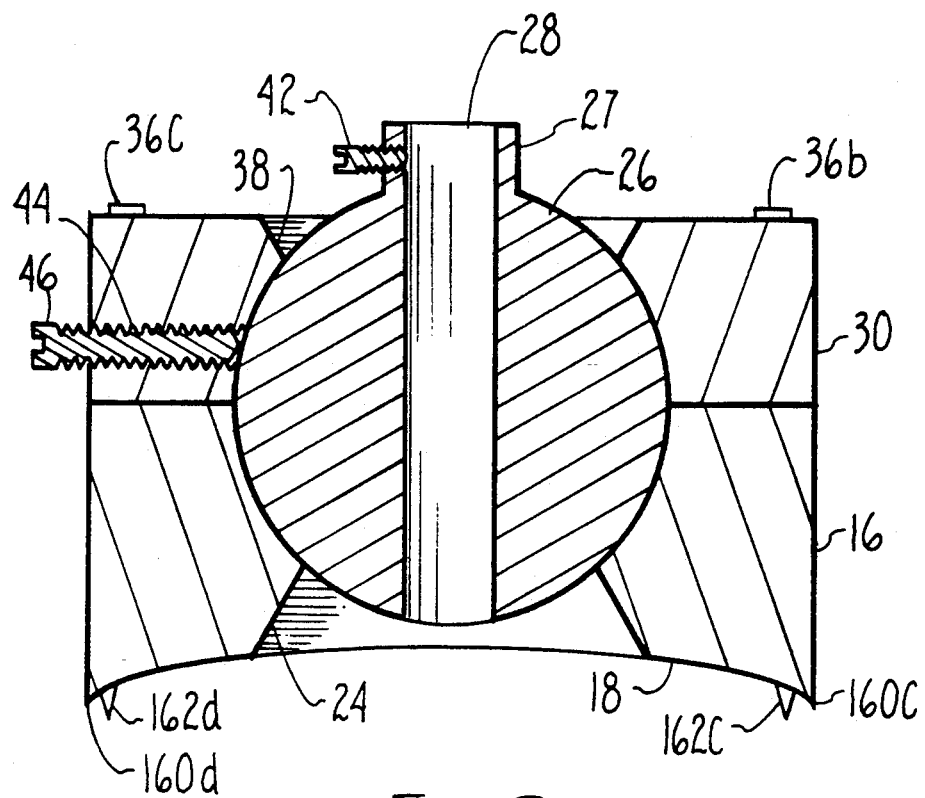
FIG. 3 is a cross-sectional view of the ball joint of the present invention, with the ball in one predetermined orientation and the neurosurgery tool removed, as seen along the line 3—3 in FIG. 1.

The details of the tool 10 can best be seen in reference to FIGS. 2 and 3. As shown in FIG. 2, the tool 10 includes an engagement member, preferably a plate 16, which can be made by any well-known means, e.g., forging, molding, or casting, that is suitable for the type of material that constitutes the plate 16. Preferably, the plate 16 is made of a rigid, strong, wear-resistant biocompatible material, such as stainless steel or hard plastic. The plate 16 has a bottom surface 18 which is configured to conform to the skull of the patient 12.

Also, FIG. 2 shows that the plate 16 has a top surface 20, and a concave socket 22 is formed in the top surface 20. The socket 22 is shaped as a portion of a hemisphere, and can be machined into the top surface 20 or formed during the molding, forging, or casting of the plate 16. Further, a channel 24 is formed in the plate 16 between the bottom surface 18 and the socket 22. Thus, the socket 22 is in communication with the channel 24. Preferably, as shown best in FIG. 3, the walls of the channel 24 are tapered outwardly from the socket 22 to the bottom surface 18 of the plate 16.

In cross-reference to FIGS. 2 and 3, four bottom corners 160a, 160b, 160c, 160d (corners 160a, 160b shown in FIG. 2 and corners 160c, 160d shown in FIG. 3) of the plate 16 are preferably sharpened, for gripping the skull of the patient 12 and thereby preventing sliding of the plate 16 on the skull. Additionally, four small spikes 162a, 162b, (FIG. 2) and 162c, 162d (FIG. 3) can be attached to the corners 160a, 160b, 160c, 160d of the plate 16 to increase the propensity of the plate 16 to grip the skull of the patient 12. It is to be understood that the spikes 162a, 162b, 162c, 162d can be used in lieu of sharpening the corners 160a, 160b, 160c, 160d of the plate 16.

FIGS. 2 and 3 also show that the orientation tool 10 includes a probe guiding member that is operably engaged with the engagement member for holding the probe 14. More particularly, FIGS. 2 and 3 show that in one presently preferred embodiment, the probe guiding member is a substantially spherical ball 26 which fits snugly within the socket 22 and which can rotate within the socket 22. As was the case with the plate 16, the ball 26 is made of a rigid, strong, wear-resistant, biocompatible material, such as stainless steel or hard plastic.

The ball 26 has a collar 27 formed integrally therewith, and a generally cylindrical bore 28 is formed in the ball 26 and collar 27 during manufacture for receiving the neurosurgery probe 14. Alternatively, the bore 28 can be drilled into the ball 26. Preferably, the bore 28 has a diameter that is slightly larger than the diameter of the neurosurgery probe 14. Consequently, slidable motion of the probe 14 within the bore 28 is permitted. Also, the bore 28 radially supports the probe 14. Further, it may now be appreciated that the diameter of the channel 24 and the taper of the channel 24 are established to permit the ball 26 to be rotated through relatively wide arcs, while providing sufficient clearance during rotation between the walls of the channel 24 and the probe 14 (FIG. 1), which extends through the channel 24 into the skull of the patient 12.

Still referring to FIGS. 2 and 3, a retainer ring 30 is engageable with the plate 16 to hold the ball 26 in the socket 22. The retainer ring 30 is formed with four holes 32a-d, and the plate 16 is formed with four plate holes 34a-d. Four threaded fasteners 36a-d extend through respective holes 32a-d and are threadably engaged with the plate holes 34a-d to hold the retainer ring 30 onto the plate 16. Thus, the retainer ring 30 can be removably attached to the plate 16. It is to be understood that other suitable means for connecting the ring 30 and plate 16, e.g., clips, (not shown) can be provided in place of the fasteners 36a-d.

FIGS. 2 and 3 also show that the retainer ring 30 has an annular bevel ring 38. The bevel ring 38 has a diameter that is less than the diameter of the ball 26. Consequently, the ball 26 cannot pass through the bevel ring 38, and is accordingly retained within the socket 22 of the plate 16 when the retainer ring 30 is positioned over the ball 26 and attached to the plate 16.

The present invention includes a fastening member for preventing relative motion between the ball 26 and the neurosurgery probe 14, and a locking member for preventing relative motion between the ball 26 and the plate 16. In one presently preferred embodiment, the fastening member is a set screw 42 and the locking member is a set bolt 46.

More specifically, as shown in FIGS. 2 and 3, the collar 27 of the ball 26 has a threaded orifice 40 formed therein which extends from the surface of the collar 27 to the bore 28, and a set screw 42 is threadably engageable with the orifice 40 and can be rotated to cause the set screw 42 to extend into the bore 28. Thus, once the neurosurgery probe 14 (shown in FIG. 1) is positioned in the bore 28 as desired, the set screw 42 can be tightened to urge against the neurosurgery probe 14 and thereby hold the probe 14 stationary within the bore 28. Accordingly, it may now be appreciated that the purpose of the collar 27 is to establish a more effective orifice 40 than would otherwise be established if the orifice were instead formed in the spherical portion of the ball 26.

Additionally, as best shown in FIG. 3, the retainer ring 30 has a threaded aperture 44 formed therein which extends from the outer surface of the retainer ring to the socket 38. A set bolt 46 is threadably engageable with the aperture 44 and can be rotated to cause the set bolt 46 to extend into the socket 38. Thus, once the ball 26 is oriented in the socket 22 as desired, the set bolt 46 can be tightened to urge against the ball 26 and thereby hold the ball 26 stationary within the socket 22.

Figure 4:
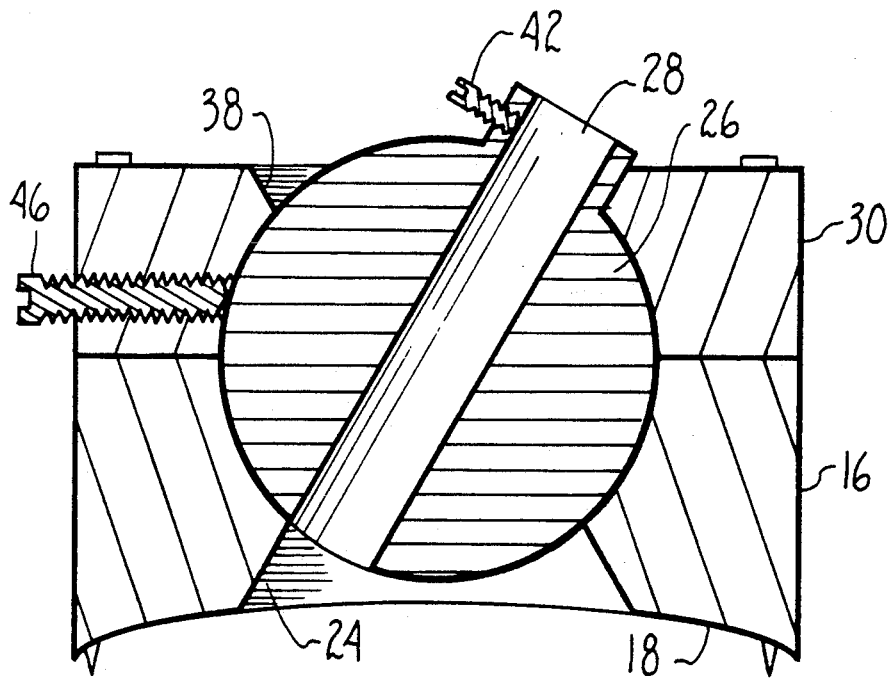
FIG. 4 is a cross-sectional view of the ball joint of the present invention, with the ball in another predetermined orientation and the neurosurgery tool removed, as would be seen along the line 4—4 in FIG. 1.

The operation of the orientation tool 10 can be appreciated in reference to FIGS. 1, 3, and 4. After an entry hole has been drilled into the skull of the patient 12, the plate 16 is positioned on the patient's skull with the bottom surface 18 of the plate 16 generally conforming the to skull of the patient 12. Also, the plate 16 is positioned on the skull of the patient 12 with the channel 24 of the plate 16 juxtaposed (i.e., directly over) the hole which has been drilled in the skull of the patient 12.

Next, the ball 26 is positioned in the socket 22, and the retainer ring 30 positioned over the ball 26 and fastened to the plate 16 to hold the ball 26 within the socket 22. The ball 30 is then oriented within the socket 22 as desired by appropriately rotating the ball 26. Stated differently, the ball 26 is rotated in the socket 22 to establish a predetermined orientation of the bore 28 relative to the skull of the patient 12. For example, the ball 26 can be rotated to the orientation shown in FIG. 3, or the orientation shown in FIG. 4, or any other suitable orientation.

When the ball 26 has been properly oriented within the socket 22, the set bolt 46 is advanced inwardly to urge against the ball 26 and thereby hold the ball 26 stationary within the socket 22. Then, the neurosurgery probe 14 is advanced through the bore 28 of the ball 26 and the channel 24 of the plate 16 into the skull of the patient 12. When the probe 14 has been positioned as desired, the set screw 42 is rotated to urge against the probe 14 and thereby hold the probe 14 stationary within the bore 28.

While the particular orientation tool for neurosurgery as herein shown and described in detail is fully capable of achieving the objects of the present invention, it is to be understood that other equivalent structures are fully contemplated by the present invention, and that the present invention is accordingly to be limited by nothing other than the appended claims.

I claim:

1. An orientation tool for selectively supporting a neurosurgery probe in a predetermined orientation relative to the skull of a patient, comprising:
   a plate having a top surface and a non-flat bottom surface generally conforming to the shape of the skull, the plate having a socket formed in said top surface and a channel formed between said socket and said bottom surface;
   a ball in rotatable engagement with the socket, the ball having a bore formed therethrough in communication with said channel, said bore being configured for closely receiving the neurosurgery probe in slidable engagement therewith; and
   means for holding said ball in said socket.

2. The tool of claim 1, wherein the socket is shaped as a portion of a sphere and the ball fits snugly within the socket.

3. The tool of claim 1, wherein the channel of the plate is tapered outwardly toward the bottom surface of the plate.

4. The tool of claim 1, further comprising an orifice formed in the ball and a fastening member threadably engaged with the orifice for selectively contacting the neurosurgery probe to thereby prevent motion of the probe relative to the ball.

5. The tool of claim 1, further comprising four spikes formed on the bottom surface of said plate and extending outwardly therefrom for gripping the skull.

6. The tool of claim 1, wherein said holding means is a retainer ring attached to the plate.

7. The tool of claim 6, further comprising an aperture formed in the retainer ring and a locking member threadably engaged therewith for selectively contacting the ball to hold the ball stationary with respect to the retaining ring.

8. The tool for supporting a neurosurgery probe, comprising:
   a ball having a bore formed therethrough for radially supporting the neurosurgery probe;
   a plate having a curved bottom surface for conforming to a human skull and a socket for receiving and supporting the ball, the plate establishing a channel between the bore of the ball and the skull; and
   means for holding the ball in rotatable contact with the plate.

9. The tool recited in claim 8, wherein the channel of the plate is tapered outwardly toward the bottom surface of the plate.

10. The tool recited in claim 8, further comprising an orifice formed in the ball and a screw threadably engaged with the orifice for selectively contacting the neurosurgery probe to thereby prevent motion of the probe relative to the ball.

11. The tool recited in claim 8, wherein said holding means is a retainer ring attached to the plate and the tool further comprises an aperture formed in the ring and a bolt threadably engaged therewith for selectively contacting the ball to hold the ball stationary with respect to the ring.

12. The tool recited in claim 8, further comprising four spikes formed on said plate and extending outwardly therefrom for gripping the skull.

13. A method for supporting a neurosurgery probe in a predetermined orientation during surgery on a patient, comprising:
   providing a ball having a bore formed therethrough;
   providing a plate having a socket and a non-flat bottom surface conformed to the patient's skull;
   rotatably engaging the ball with the socket;
   moving the ball as appropriate to establish a predetermined orientation of the bore relative to the patient's skull; and
   engaging the probe within the bore.

14. The method of claim 13, further comprising the step of holding the ball in the predetermined orientation.

15. The method of claim 13, further comprising the step of holding the neurosurgery probe stationary with respect to the bore.

16. The method of claim 13, further comprising the step of preventing slidable motion of the plate on the skull.

* * * * *